US00PP08952P

United States Patent [19]

Marciel et al.

[11] Patent Number: Plant 8,952

[45] Date of Patent: Oct. 25, 1994

[54] HYBRID TEA ROSE PLANT NAMED DEVSTAR

[75] Inventors: Stanley G. Marciel; Jeanne A. Marciel, both of Aptos, Calif.

[73] Assignee: DeVor Nurseries, Inc., Watsonville, Calif.

[21] Appl. No.: 148,827

[22] Filed: Nov. 4, 1993

[51] Int. Cl.[5] ..... A01H 5/00

[52] U.S. Cl. ..... Plt./14

[58] Field of Search ..... Plt. 14, 15

*Primary Examiner*—Howard J. Locker

*Attorney, Agent, or Firm*—Christie, Parker & Hale

[57] ABSTRACT

A new hybrid tea rose plant producing white flowers.

1 Drawing Sheet

SUMMARY OF THE INVENTION

The present invention relates to a new and distinct variety of rose plant of the hybrid tea rose class which was originated by my crossing as seed parent the variety known as 'Coquette' (U.S. Plant Pat. No. 4,019) and as pollen parent an unnamed and unpatented seedling of my creation (64022-39). The varietal denomination of this new rose is 'Devstar'.

Among the novel characteristics possessed by this new variety which distinguish it from its parents and all other varieties of which I am aware are its attractive well formed white flowers borne on a plant particularly suitable for use for cut-flower production in greenhouses. Flowers, which are borne on long, strong stems, are of good cut-flower quality.

Asexual reproduction by budding of the new variety as performed in Watsonville, Calif. shows that the foregoing and other distinguishing characteristics come true to form and are established and transmitted through succeeding propagations.

BRIEF DESCRIPTION OF ILLUSTRATIONS

The accompanying illustration shows typical specimens of the vegetative growth and flowers of the new variety in different stages of development and depicted in color as nearly true as it is reasonably possible to make the same in a color illustration of this character.

DESCRIPTION OF THE NEW VARIETY

Parentage: Seedling.

*Seed parent.*—'Coquette'.

*Pollen parent.*—Unnamed seedling (64022-39).

Class: Hybrid tea.

The following is a detailed description of my new variety, of new specimens grown under glass in Watsonville, Calif., in the month of September. The color terminology used is in accordance with The Royal Horticultural Society Colour Chart (RHSCC), and refers to plate numbers in the aforementioned color chart. Phenotypic expression may vary depending on light, environmental and cultural conditions.

FLOWER

Blooming habit: Continuous.

A. Bud:

(1) *Size.*—Medium.

(2) *Form.*—Pointed and tapering.

(3) *Color.*—Before sepals divide, bud color is near 145C to B.

(4) *Sepals.*—Upright, covering bud, then spreading and reflexing; some sepals are foliaceous. Color: Green with reddish cast.

(5) *Peduncle.*—Length: About 14–16 cm. Aspect: Straight. Strength: Erect, sturdy. Color: Near 144A to B.

(6) *Bracts.*—From 1 to 2; broadly elliptical with acute tip, 10–13 cm below calyx; near 137A.

B. Bloom:

(1) *Size.*—Average size when fully expanded — about 11 to 13 cm.

(2) *Borne.*—Singly, one to a stem.

(3) *Form.*—Generally ovoid with petal slightly reflexing.

(4) *Petalage.*—Number of petals under normal conditions — about 48 to 53.

(5) *Color.*—$\frac{1}{3}$ to $\frac{1}{2}$ open: top surface of outer petals is near 155D to near 157A toward petal base; undersurface of outer petals is near 155D to near 157C toward base; top surface of inner petals is near 155D with near 1C at very tip of base; undersurface of inner petals is near 155B to D with near 1C at very tip of base; color at point of petal attachment is near 1C and the general tonality from a distance is white. Fully open blooms: top surface of outer petals is near 155D with near 157C toward petal base; undersurface of outer petals is near 155D to near 157D toward base; top surface of inner petals is near 155D with near 157C toward base; undersurface of inner petals is near 155D with near 157D toward base; color at point of petal attachment is near 157C and the general tonality from a distance is white. Color of bloom upon aging becomes a purer white, with the petal top surface near 155D and the petal undersurface also near 155D.

C. Petals:

(1) *Texture.*—Medium.

(2) *Appearance.*—Inside and outside are smooth.

(3) *Form.*—Smooth, slightly reflexing.

(4) *Arrangement.*—Regularly arranged, imbricated and informal at maturity.

(5) *Petaloids.*—Many.

(6) *Fragrance.*—None.

(7) *Lasting quality.*—Very long on plant and 8–10 days as cut flower; moderate petal drop.

REPRODUCTIVE ORGANS

A. Stamens:
(1) *Color.*—Near 19A.
(2) *Arrangement.*—Regularly arranged, slightly antrorse.
(3) *Anthers.*—Color near 19A.
(4) *Filaments.*—Color near 1C.
(5) *Pollen.*—Color near 22A.

B. Pistils
(1) *Styles.*—Bunched, medium length, thin.
(2) *Stigmas.*—Color near 179C with near 60A below.

C. Characteristics of hips: Not observed.

PLANT

A. Form: Upright.

B. Growth: Vigorous, uniform branching; height attained about 274–305 cm at first season. C. Foliage: Compound 3–5 leaflets.
(1) *Size.*—Large.
(2) *Quantity.*—Abundant.
(3) *Color.*—New foliage — upper side purple, underside purple; mature foliage — upper side near 147A, underside near 147B.
(4) *Shape.*—Terminal leaflet is oblong, other leaflets oval.
(5) *Texture.*—Semi-glossy, smooth.
(6) *Edge.*—Serrate.
(7) *Serration.*—Denticulate.
(8) *Leaf stem.*—Color — medium green.
(9) *Stipules.*—Medium length, hairy, adnate.
(10) *Rachis.*—Smooth with occasional prickle.
(11) *Petioles.*—Top near 147C, underside near 147C.
(12) *Auricle.*—Slender with small hairs.
(13) *Resistance to disease.*—Under greenhouse conditions no rust and blackspot; good resistance to mildew.

D. Wood
(1) *New wood.*—Color near 146B, bark smooth.
(2) *Old wood.*—Color near 146A, bark smooth.

E. Flower Stem: About 83–89 cm from last cut.

F. Thorns:
(1) *Thorns.*—Quantity: on main stalk, few; on laterals from stalk, few. Form: Slightly curved downward, thin. Length: Medium. Color: Near 166B at base with near 146D at tip. Position: Irregular.
(2) *Prickles.*—Few.

G. Winter hardiness: Greenhouse variety; wintered well in California.

I claim:

1. A new and distinct variety of rose plant of the hybrid tea rose class, substantially as shown and described.

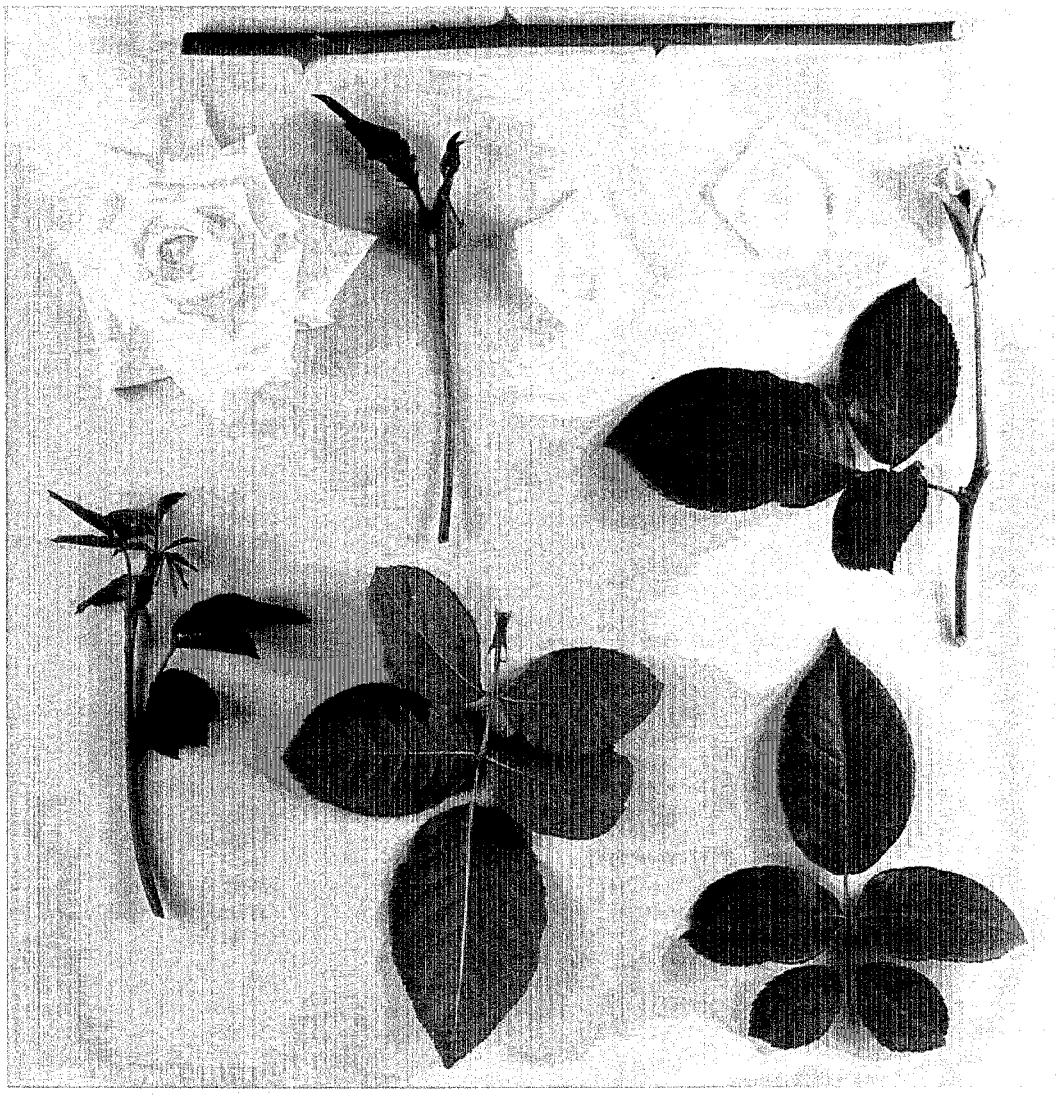

* * * * *